United States Patent [19]
Enomoto

[11] Patent Number: 5,147,803
[45] Date of Patent: Sep. 15, 1992

[54] METHOD AND COMPOSITION FOR STABILIZING BLOOD COAGULATION FACTORS AND BLOOD CONTROL PLASMAS CONTAINING THE COMPOSITION

[75] Inventor: Masayasu Enomoto, Takatsuki, Japan

[73] Assignee: Nippon Shoji Kabushiki Kaisha, Osaka, Japan

[21] Appl. No.: 406,247

[22] Filed: Sep. 12, 1989

[30] Foreign Application Priority Data

Sep. 12, 1988 [JP] Japan ................................. 63-227940

[51] Int. Cl.$^5$ ...................... G01N 31/72; G01N 31/86
[52] U.S. Cl. ........................................ 436/16; 436/63; 436/69; 436/176
[58] Field of Search ..................... 436/8–19, 436/63, 69, 176; 514/2

[56] References Cited

U.S. PATENT DOCUMENTS 3,323,995  6/1967  Lorand .
4,056,484  11/1977  Heimburger et al. ................. 436/16
4,271,122  6/1981  Strässle et al. ......................... 436/16
4,624,927  11/1986  Fukushima et al. ................... 436/16
4,784,944  11/1988  Kolde ..................................... 435/13
4,959,175  9/1990  Yatzidis ................................... 514/2

FOREIGN PATENT DOCUMENTS 37078    10/1981  European Pat. Off. .
117064   8/1984   European Pat. Off. .
359201   3/1990   European Pat. Off. .
1227414  2/1962   Fed. Rep. of Germany .
57-112367 7/1982  Japan .

*Primary Examiner*—James C. Housel
*Assistant Examiner*—William Chan
*Attorney, Agent, or Firm*—Wegner, Cantor, Mueller & Player

[57] ABSTRACT

Blood coagulation factors are stabilized by addition of glycylglycine and/or glycylglycylglycine to blood or plasma in such an amount that they have no effect on a blood coagulation time.

12 Claims, No Drawings

METHOD AND COMPOSITION FOR STABILIZING BLOOD COAGULATION FACTORS AND BLOOD CONTROL PLASMAS CONTAINING THE COMPOSITION

FIELD OF THE INVENTION

The present invention relates to a method for stabilizing blood coagulation factors.

BACKGROUND OF THE INVENTION

It has been known that blood coagulation includes both endogenous and extrinsic reactions and many coagulation factors participate in these reactions. And, accurate determination of their reactions in a sample is one of important items of clinical tests. However, many of these coagulation factors are protein and liable to be denaturated. Among them, particularly, V and VIII factors are known to be those readily inactivated. In many cases, instability of the factors causes trouble in clinical tests. For example, it has been said that a sample to be subjected to a coagulation test should be kept at 2° to 8° C. and the test should be done within 4 hours after blood collection. Further, a commercially available control plasma (lyophilized product) to be used in the test is stable for only one day under refrigeration after reconstitution thereof Stabilities of various coagulation factor deficient plasma to be used as test reagents are very low and many of them are stable for only several hours under refrigeration and should not be frozen.

If such unstable blood coagulation factors can be stabilized, it is possible to ease restriction of storage conditions and shelf life of a sample after blood collection, control plasma and various coagulation factor deficient plasma This is very advantageous in view of clinical tests as well as industrial purposes. Thus, there has been requested to develop a method for stabilizing blood coagulation factors.

On the other hand, many studies on stabilization of various proteins including enzymes have been done. However, substances which exhibit stabilization effects on proteins are quite different from each other according to kinds and origins of proteins and, at present, respective specific substances are independently found for stabilizing respective proteins.

Regarding stabilization of blood coagulation factors, there have been proposed coagulation factor preparations of certain factors, for example, VIII, IX and XIII factors, wherein these factors are stabilized by using albumin, dextran, sugars, amino acids, organic carboxylic acids and neutral salts such as NaCl, KCl and the like (Japanese Patent Kokai Nos. 56-127308, 56-135418, 58-74617, 59-134730, 60-199829, 61-60614, 62-10019 and 62-195331). However, they are aimed at stabilizing the coagulation factors during heat treatment for inactivation of viruses in the preparations and, therefore, they are added in very high concentrations. In a blood coagulation test, if such a substance, e.g., an amino acid such as glycine, alanine or the like is added to blood or plasma in a high concentration, for example, 10% or more, the coagulation reaction itself is inhibited and the desired coagulation test can not be carried out. Further, the above proposal is limited to only certain coagulation factors and the preparations do not contain many other blood components. Thus, the proposal is not directed to plasma or blood wherein all or a part of factors participated in coagulation reactions are contained or a part of them are deficient.

The present inventors have studied intensively to find out a method for stabilizing many blood coagulation factors contained in blood or plasma which does not unfavorably affect a coagulation reaction. As the result, it has been found that the coagulation factors can be remarkably stabilized by adding the dipeptide, glycylglycine and/or the tripeptide, glycylglycylglycine to blood or plasma.

OBJECTS OF THE INVENTION

The main object of the present invention is to provide a method for stabilizing blood coagulation factors.

This object as well as other objects and advantages of the present invention will become apparent to those skilled in the art from the following description.

SUMMARY OF THE INVENTION

According to the present invention, there is provided a method for stabilizing blood coagulation factors which comprises adding glycylglycine and/or glycylglycylglycine to blood or plasma in such an amount that they have no influence on a blood coagulation time.

The present invention further provides a control plasma which comprises as a stabilizer of blood coagulation factors glycylglycine and/or glycylglycylglycine in such an amount that they have no influence on a blood coagulation time.

In addition, the present invention provides a reagent for determination of biological activity of blood coagulation factors which comprises as a stabilizer of blood coagulation factors glycylglycine and/or glycylglycylglycine in such an amount that they have no influence on a blood coagulation time.

DETAILED DESCRIPTION OF THE INVENTION

Glycylglycine and glycylglycylglycine to be used in the present invention are peptides wherein two and three amino acids are bonded, respectively, and they are different from the substances used in known stabilization methods. It has not been known heretofore in the prior art that these substances are useful for stabilizing not only certain coagulation factors but also all coagulation factors.

Blood coagulation factors are divided into those involved in an endogenous coagulation reaction pathway whose coagulation reaction is started by contact with a surface of a foreign substance, and those involved in an extrinsic coagulation reaction pathway whose coagulation reaction is started by tissue thromboplastin. The present invention aims at stabilizing all factors involved in both reaction pathways and these factors are stabilized by addition of glycylglycine and/or glycylglycylglycine to blood or plasma.

That is, the stabilization method of the present invention is carried out by addition of glycylglycine, glycylglycylglycine, or both to a system to be stabilized. A concentration of these substances, is for example, 0.1 to 2.0% (w/v), preferably, 0.5 to 1.0% (w/v) in the case that a system to be stabilized is blood (whole blood). When the concentration is less than 0.1%, no stabilization effect is expected. On the other hand, a slight hemolysis is observed at the concentration of 1.5% and hemolysis becomes more significant as the concentration is increased. Further, a coagulation time [prothrombin time (PT) or activated partial thromboplastin time (APTT)] also tends to e prolonged gradually at a concentration of 1.5% or higher. Therefore, a concentration of more than 2% is undesirable. When both substances are used together, an amount of each substance can be appropriately chosen and the above-defined concentration corresponds to the sum of them. In the case that a system to be stabilized is plasma, the concentration is 0.1 to 4.0% (w/v), preferably, 0.5 to 2.0% (w/v). When the concentration is less than 0.1%, no stabilization effect is expected. Although a coagulation time is gradually prolonged at the concentration of 2.0% or higher, stabilization effect is still observed. Depending upon the purpose of stabilization, the concentration of up to 4.0% (w/v) causes no problem. When the concentration becomes more than 4.0%, the coagulation time becomes too long and it is undesirable. Likewise, in the case of plasma, when both substances are used together, an amount of each substance can be appropriately chosen and the above-defined concentration corresponds to the sum of them.

In order to carry out the method of the present invention, glycylglycine and/or glycylglycylglycine are added to blood, for example, together with a substance used as an anticoagulant when blood is collected, or added to blood by dissolving them in a solution of an anticoagulant. Alternatively, glycylglycine and/or glycylglycylglycine can be added to blood wherein an anticoagulant has been already added. Examples of the anticoagulant used for collection of blood include sodium citrate, oxalic acid, EDTA and the like. Glycylglycine and/or glycylglycylglycine in the form of solids or an aqueous solution can be also added to plasma obtained by centrifugation of blood wherein an anticoagulant has been already added.

The method of the present invention is mainly employed at the time of collecting blood from a patient at a place where a coagulation test is carried out, or after collection of blood from a patient to carry out a coagulation test. Further, glycylglycine and/or glycylglycylglycine can be added to blood or plasma in the industrial production of control plasma and various coagulation factor deficient plasma to be used as reagents for determination of biological activity of coagulation factors. For example, they can be used in the production of normal and abnormal control plasma, various coagulation factor deficient plasma such as those deficient in I, II, V, VII, VIII, IX, X, XI, XII and XIII factors, respectively, protein C removed plasma, antithrombin III removed plasma and the like.

Thus, the present invention also provides a control plasma and a reagent for determination of biological activity of blood coagulation factors, wherein glycylglycine and/or glycylglycylglycine are contained as a stabilizer of blood coagulation factors. These control plasma and reagents can be prepared by admixing glycylglycine and/or glycylglycyl-glycine with other conventional components in the concentration as described above according to the conventional method. They can be in the form of liquid preparations, concentrated liquid preparations, freeze dried products and the like. Further, they can be in the form of kits.

According to the present invention, handling of sample plasma at a place where a clinical test is carried out becomes easy. Further, shelf life of various coagulation factor deficient plasma can be extended to minimize loss.

The following Examples further illustrate the present invention in detail but are not to be construed to limit the scope thereof.

EXAMPLE 1

Addition to plasma (1) Effect of addition of glycylglycine

Blood (9 volumes) collected from a normal person was admixed with 3.2% trisodium citrate solution (1 volume) and the mixture was centrifuged at 3,000 r.p.m. for 10 minutes to obtain plasma. To the plasma was added 0% (control) to 4% (w/v) of glycylglycine and a coagulation time was measured to determine stabilization effect on coagulation factors. Measurement of prothrombin time (PT) for determination of inactivation in extrinsic coagulation factors (II, V, VII and X) as well as activated partial thromboplastin time (APTT) for determination of inactivation in endogenous coagulation factors (XII, XI, IX, VIII, prekallikrein and high molecular kininogen) were conducted with time on the days 0, 4, 8 and 12.

The results are shown in Table 1.

The measurement of PT and APTT was conducted as follows:

PT measurement

To plasma (0.1 ml) which was previously heated at 37° C. for 2 minutes was added a thromboplastin reagent (Thrombomat manufactured by bioMerieux S.A., France) warmed to 37° C. (0.2 ml) to start a coagulation reaction and a coagulation time (seconds) was measured.

APTT measurement

Plasma (0.1 ml) and APTT reagent (Actimat manufactured by bioMerieux S.A., France) (0.1 ml) were mixed and the mixture was heated at 37° C. for 3 minutes. To this was added 25 mM calcium chloride warmed to 37° C. (0.1 ml) to start the coagulation reaction and a coagulation time (seconds) was measured.

The measurement of the coagulation time was conducted by using a blood coagulation measurement apparatus, Option 8 (manufactured by bioMérieux S.A., France) which detected the end point of coagulation by optical measurement of the change of turbidity.

TABLE 1

| Concentration (%) | Items | Effect of addition of glycylglycine (stored at 25° C.) | | | |
|---|---|---|---|---|---|
| | | Day 0 | Day 4 | Day 8 | Day 12 |
| 0 | PT | 11.4 | 14.6 | 17.9 | 22.4 |
| | APTT | 37.3 | 55.1 | 77.9 | 131.8 |
| 0.02 | PT | 11.3 | 13.7 | 16.8 | 22.1 |
| | APTT | 37.4 | 54.7 | 79.8 | 127.3 |
| 0.05 | PT | 11.3 | 14.1 | 17.4 | 23.9 |
| | APTT | 37.0 | 56.1 | 61.9 | 134.3 |
| 0.1 | PT | 11.3 | 13.5 | 15.9 | 19.7 |
| | APTT | 36.5 | 54.3 | 63.4 | 99.7 |
| 0.2 | PT | 11.1 | 12.7 | 14.8 | 19.0 |
| | APTT | 35.5 | 54.6 | 60.2 | 91.4 |
| 0.5 | PT | 11.3 | 11.8 | 12.5 | 15.2 |
| | APTT | 33.0 | 48.1 | 50.9 | 75.4 |
| 1.0 | PT | 11.5 | 12.3 | 12.7 | 14.2 |
| | APTT | 33.2 | 44.1 | 38.3 | 60.1 |
| 2.0 | PT | 12.4 | 12.6 | 11.8 | 11.9 |
| | APTT | 37.1 | 43.7 | 43.6 | 58.9 |
| 3.0 | PT | 13.5 | 13.2 | 11.7 | 11.9 |
| | APTT | 46.5 | 50.5 | 52.4 | 63.6 |
| 4.0 | PT | 14.7 | 14.5 | 12.9 | 11.9 |

TABLE 1-continued

| Concentration (%) | Effect of addition of glycylglycine (stored at 25° C.) | | | |
|---|---|---|---|---|
| | Items | Day 0 | Day 4 | Day 8 | Day 12 |
| | APTT | 58.7 | 58.3 | 51.4 | 63.6 (seconds) |

As seen from Table 1, PT of the control (glyclygly- cine 0%) was prolonged from 11.4 seconds to 22.4 seconds at 25° C. for 12 days and APTT thereof was prolonged from 37.4 seconds to 131.8 seconds. Namely, inactivation of coagulation factors was observed. Likewise, the stabilization effect was not observed at a concentration of less than 0.1%. On the other hand, the stabilization effect was observed at a concentration of more than 2%. However, the coagulation time was prolonged due to addition of glycylglycine. Namely, on the day 0, PT of the control (glycylglycine 0%) was 11.4 seconds and its APTT was 37.3 seconds. By addition of 3% of glycylglycine, PT was prolonged to 13.5 seconds and APTT was prolonged to 46.5 seconds. Due to this prolongation, a concentration of more than 4% was undesired. Regarding the addition of 1% of glycylglycine, PT was prolonged from 11.5 seconds to 14.2 seconds at 25° C. for 12 days and APTT was prolonged from 33.2 seconds to 60.1 seconds. However, in comparison with the control, this prolongation was minor and it was recognized that inactivation of coagulation factors was inhibited.

According to these coagulation times, it is considered that, in comparison with the control, coagulation factors are stabilized by 3 times or more with respect to PT and 2 times or more with respect to APTT.

(2) Effect of addition of glycylglycylglycine

According to the same manner as in Example 1 (1), PT and APTT were measured to determine the effect of addition of glycylglycylglycine.

The results are shown in Table 2.

TABLE 2

| Concentration (%) | Effect of addition of glycylglycylglycine (stored at 25° C.) | | | |
|---|---|---|---|---|
| | Items | Day 0 | Day 4 | Day 8 | Day 12 |
| 0 | PT | 10.5 | 13.6 | 16.1 | 21.9 |
| | APTT | 29.9 | 43.7 | 54.5 | 101.1 |
| 0.02 | PT | 10.4 | 13.1 | 15.5 | 21.3 |
| | APTT | 29.8 | 45.0 | 56.0 | 109.5 |
| 0.05 | PT | 10.4 | 13.4 | 15.7 | 22.3 |
| | APTT | 28.3 | 43.4 | 40.5 | 93.5 |
| 0.1 | PT | 10.2 | 12.8 | 14.5 | 20.1 |
| | APTT | 28.1 | 44.1 | 39.2 | 81.5 |
| 0.2 | PT | 10.4 | 12.5 | 14.1 | 18.9 |
| | APTT | 27.3 | 40.2 | 42.8 | 77.5 |
| 0.5 | PT | 10.5 | 12.3 | 13.2 | 14.4 |
| | APTT | 26.2 | 37.8 | 37.9 | 51.8 |
| 1.0 | PT | 10.8 | 11.4 | 11.6 | 13.1 |
| | APTT | 25.8 | 37.0 | 38.8 | 45.7 |
| 2.0 | PT | 12.0 | 12.5 | 11.0 | 11.7 |
| | APTT | 29.4 | 37.5 | 40.8 | 43.1 |
| 3.0 | PT | 13.2 | 12.1 | 11.1 | 12.1 |
| | APTT | 36.8 | 40.4 | 43.4 | 58.2 |
| 4.0 | PT | 14.3 | 13.0 | 14.8 | 16.7 |
| | APTT | 46.0 | 44.5 | 39.6 | 54.7 (seconds) |

As seen from Table 2, PT of the control (glycylglycylglycine 0%) was prolonged from 10.5 seconds to 21.9 seconds at 25° C. for 12 days and APTT thereof was prolonged from 29.9 seconds to 101.1 seconds. On the other hand, regarding the addition of 1% of glycylglycylglycine, PT was prolonged from 10.8 seconds to 13.1 seconds and APTT was prolonged from 25.8 seconds to 45.7 seconds. In comparison with the control, this prolongation was minor and it was recognized that inactivation of coagulation factors was inhibited. The stabilization effect was not observed at a concentration of less than 0.1%. Due to the prolongation, a concentration of more than 4% was undesired.

According to these coagulation times, it is considered that, in comparison with the control, coagulation factors are stabilized by 3 times or more with respect to PT and 2 times or more with respect to APTT.

According to these results, it is clear that glycylglycine and glycylglycylglycine are useful for stabilizing all blood coagulation factors in plasma.

EXAMPLE 2

Addition to blood (1) Effect of addition of glycylglycine

Blood (9 volumes) collected from a normal person was admixed with 3.2% trisodium citrate (1 volume) and to the resulting whole blood was added glycylglycine. After dissolution, the mixture was centrifuged at 3,000 r.p.m. for 10 minutes to obtain plasma. As controls, after centrifugation of the same whole blood to obtain plasma, glycylglycine was added to the plasma. According to the same manner as in Example 1, effects on coagulation times (PT and APTT) were determined.

The results are shown in Table 3.

TABLE 3

| Glycylglycine (% w/v) | | Whole blood (second) | Plasma (second) | Hemolysis of whole blood |
|---|---|---|---|---|
| 0 | PT | 10.2 | 10.3 | no hemolysis |
| | APTT | 26.6 | 26.3 | |
| 0.2 | PT | 10.0 | 10.2 | no hemolysis |
| | APTT | 25.6 | 24.8 | |
| 0.5 | PT | 10.3 | 10.4 | no hemolysis |
| | APTT | 24.7 | 24.7 | |
| 1.5 | PT | 11.6 | 11.4 | slight hemolysis |
| | APTT | 26.2 | 27.0 | |
| 4.0 | PT | 15.0 | 13.8 | strong hemolysis |
| | APTT | 46.9 | 42.9 | |

As seen from Table 3, when 4.0% of glycylglycine was added to whole blood, strong hemolysis was observed and coagulation times were prolonged. This prolongation was considered to be resulted from hemolysis. Almost the same stabilization effect as that in Example 1 was observed.

(2) Effect of addition of glycylglycylglycine

According to the same manner as in Example 2 (1), glycylglycylglycine was added to whole blood and the effect thereof on coagulation times (PT and APTT) were determined.

The results are shown in Table 4.

TABLE 4

| Glycylglycylglycine (% w/v) | | Whole blood (second) | Plasma (second) | Hemolysis of whole blood |
|---|---|---|---|---|
| 0 | PT | 11.1 | 11.2 | no hemolysis |
| | APTT | 36.5 | 35.0 | |
| 0.2 | PT | 11.2 | 11.2 | no hemolysis |
| | APTT | 36.2 | 34.3 | |
| 0.5 | PT | 11.3 | 11.4 | no hemolysis |

TABLE 4-continued

| Glycyl-glycyl-glycine (% w/v) | | Whole blood (second) | Plasma (second) | Hemolysis of whole blood |
|---|---|---|---|---|
| | APTT | 35.6 | 33.8 | |
| 1.5 | PT | 12.6 | 12.6 | slight |
| | APTT | 36.3 | 36.7 | hemolysis |
| 4.0 | PT | 16.6 | 15.8 | strong |
| | APTT | 63.7 | 64.6 | hemolysis |

As seen from Table 4, when 4.0% of glycylglycylglycine was added to whole blood, strong hemolysis was observed. Almost the same stabilization effect as that in Example 1 was observed.

EXAMPLE 3

Effect of using combination of glycylglycine and glycylglycylglycine

After thawing commercially available frozen plasma at room temperature, it was centrifuged at 3,000 r.p.m. for 10 minutes to remove precipitates. To the resulting plasma was added a mixture of glycylglycine and glycylglycylglycine in the proportion of 3:0, 2:1, 1:2 or 0:3 so that the concentration of the mixture in the plasma became 1.5% (w/v) and the mixture was dissolved.

According to the same manner as described in Example 1, coagulation times (PT and APTT) were measured by using plasma without addition of glycylglycine and glycylglycylglycine as a control to determined the effect of combination of these substances.

The results are shown in Table 5.

TABLE 5

Effect of combination (stored at 25° C.)

| Glycylglycine: glycyl-glycylglycine | Day 0 | | Day 6 | | Day 10 | |
|---|---|---|---|---|---|---|
| | PT | APTT | PT | APTT | PT | APTT |
| Control (no addition) | 12.4 | 36.9 | 15.2 | 45.6 | 17.4 | 89.4 |
| 3:0 | 13.2 | 38.6 | 13.2 | 37.6 | 13.0 | 38.6 |
| 2:1 | 12.9 | 38.0 | 13.3 | 37.3 | 13.3 | 37.0 |
| 1:2 | 12.9 | 36.3 | 13.1 | 36.6 | 12.5 | 38.9 |
| 0:3 | 12.7 | 36.7 | 13.0 | 37.0 | 13.7 | 37.6 |

(seconds)

As seen from Table 5, the stabilization effect was observed by combining glycylglycine and glycylglycylglycine (2:1 or 1:2) as well as using these substances alone (3:0 or 0:3).

EXAMPLE 4

0.5% (w/v) of glycylglycine was added to antithrombin III (AT III) removed plasma to used in the determination of biological activity of antithrombin III (PCT/JP89/00173) and stability thereof was determined as follows.

The AT III removed plasma as frozen and stored in a freezer. It was thawed on each day of measurement.

Instead of a specimen (AT III), Michaelis buffer 50 μl) was added to AT III removed plasma (100 μl) and the resulting mixture was incubated at 37° C. for 2 minutes. Separately, commercially available PT reagent was diluted 10 times with 25 mM calcium chloride solution containing 10 U/ml of heparin to obtain a reaction starting solution. This solution warmed to 37° C. (200 μl) was added to the above plasma and the coagulation time was determined.

The results are shown in Table 6.

TABLE 6

Stabilization of AT III removed plasma

| Sample | Day 0 | Day 1 | Day 4 | Day 7 |
|---|---|---|---|---|
| No addition | 29.1 | 35.9 | 40.4 | 77.4 |
| Glycylglycine 0.5% | 28.9 | 32.5 | 29.4 | 28.1 |

(seconds)

As seen from Table 6, when glycylglycine was not added, the coagulation time was prolonged from 29.1 seconds to 77.4 seconds during 7 days. On the other hand, when 0.5% of glycylglycine was added, no prolongation of coagulation time was observed and remarkable stabilization effect was observed.

This shows that the properties of the reagent are maintained stably.

EXAMPLE 5

This Example was carried out for studying whether or not the remarkable stabilization effect on coagulation factors of glycylglycine and glycylglycylglycine as shown in Examples 1 to 4 were obtained by amino acids and sugars.

0.5% (w/v) of glycine, alanine or sodium aspartate or 1.0% (w/v) of mannitol, maltose or sucrose was added to commercially available stored plasma and compared with a control (without addition) and glycylglycine (0.5%). In this Example, freezing and thawing were repeated every day to determine stability.

The results are shown in Table 7.

TABLE 7

Comparison of effects of addition of various substances

| Substance | Day 0 | | Day 7 | | Day 14 | |
|---|---|---|---|---|---|---|
| | PT | APTT | PT | APTT | PT | APTT |
| Control | 13.1 | 47.9 | 14.1 | 52.9 | 17.6 | >70 |
| Glycylglycine 0.5% | 13.3 | 45.6 | 13.0 | 45.2 | 13.8 | 53.0 |
| Glycine 0.5% | 13.0 | 47.0 | 13.3 | 52.0 | 14.9 | >70 |
| Alanine 0.5% | 13.1 | 47.6 | 13.5 | 52.4 | 15.2 | >70 |
| Sodium aspartate 0.5% | 13.0 | 50.9 | 13.6 | 56.6 | 15.9 | >70 |
| Mannitol 1.0% | 13.2 | 47.2 | 14.1 | 53.2 | 16.8 | >70 |
| Maltose 1.0% | 13.6 | 47.8 | 14.4 | 54.9 | 17.7 | >70 |
| Sucrose 1.0% | 13.6 | 48.4 | 14.1 | 54.1 | 16.7 | >70 |

(seconds)

As seen from Table 7, glycylglycine showed remarkable stabilization in comparison with the control. However, in the case of the other substances, APTT was more than 70 seconds on the 14th day and the same as that of the control. Thus, no stabilization effect was observed. Further, although a slight stabilization effect was observed in the case of using amino acids, the effect was not so significant as that of glyclyglycine.

Thus, it is recognized that the stabilization effect of glycylglycine and glycylglycylglycine is specific.

What is claimed is:

1. A method for stabilizing blood coagulation factors which comprises adding a stabilizer selected from the group consisting of glycylglycine and glycylglycylglycine to blood or plasma in a final concentration of 0.1 to 4.0% (w/v) such that the stabilizer does not substantially prolong blood coagulation time.

2. A method according to claim 1, wherein the stabilizer is added to blood in a final concentration of 0.1 to 2.0% (w/v).

3. A method according to claim 2, wherein the final concentration is 0.5 to 1.0% (w/v).

4. A method according to claim 1, wherein the final concentration is 0.5 to 2.0% (w/v).

5. A control plasma comprising:
a plasma component which contains at least one blood coagulation factor; and
a stabilizer of blood coagulation factors, selected from the group consisting of glycylglycine and glycylglycylglycine, the stabilizer being present in the control plasma in a concentration of 0.1 to 4.0% (w/v) such that the stabilizer does not substantially prolong blood coagulation time.

6. A control plasma according to claim 5, wherein the final concentration is 0.5 to 2.0% (w/v).

7. A reagent for determination of biological activity of blood coagulation factors, comprising:
a plasma component which contains at least one blood coagulation factor but which is deficient in at least one blood coagulation factor or coagulation inhibitory factor; and
a stabilizer of blood coagulation factors, selected from the group consisting of glycylglycine and glycylglycylglycine, the stabilizer being present in the preagent in a concentration of 0.1 to 4.0% (w/v) such that the stabilizer does not substantially prolong blood coagulation time.

8. A reagent according to claim 7, wherein the final concentration of the stabilizer is 0.5 to 2.0% (w/v).

9. An at least partially dehydrated control plasma comprising:
a plasma component which contains at least one blood coagulation factor; and
a stabilizer of blood coagulation factors, selected from the group consisting of glycylglycine and glycylglycylglycine, the stabilizer being present in the control plasma in an amount to give the control plasma a stabilizer concentration of 0.1 to 4.0% (w/v) upon reconstruction of the control plasma, such that the stabilizer does not substantially prolong blood coagulation time.

10. The at least partially dehydrated control plasma of claim 9, wherein the concentration of the stabilizer upon reconstitution is 0.5 to 2.0% (w/v).

11. An at least partially dehydrated reagent for determination of biological activity of blood coagulation factors, comprising:
a plasma component which contains at least one blood coagulation factor but which is deficient in at least one blood coagulation factor or coagulation inhibitory factor; and
a stabilizer of blood coagulation factors, selected from the group consisting of glycylglycine and glycylglycylglycine, the stabilizer being present in the reagent in an amount to give the reagent a stabilizer concentration of 0.1 to 4.0% (w/v) upon reconstitution of the reagent, such that the stabilizer does not substantially prolong blood coagulation time.

12. The at least partially dehydrated reagent of claim 11, wherein the concentration of the stabilizer upon reconstitution is 0.5 to 2.0% (w/v).

* * * * *